(12) United States Patent
Ferrari

(10) Patent No.: US 7,392,096 B2
(45) Date of Patent: Jun. 24, 2008

(54) MULTIFUNCTION ELECTRODE AND METHOD OF MAKING SAME

(76) Inventor: R. Keith Ferrari, 357 Riverside Dr., Franklin, TN (US) 37064

( * ) Notice: Subject to any disclaimer, the term of this patent is extended or adjusted under 35 U.S.C. 154(b) by 496 days.

(21) Appl. No.: 10/922,297

(22) Filed: Aug. 19, 2004

(65) Prior Publication Data
US 2006/0041301 A1 Feb. 23, 2006

(51) Int. Cl.
A61N 1/04 (2006.01)

(52) U.S. Cl. ........................................ 607/142
(58) Field of Classification Search ............ 607/142
See application file for complete search history.

(56) References Cited

U.S. PATENT DOCUMENTS

| | | |
|---|---|---|
| 4,054,714 A | 10/1977 | Mastrangelo |
| 4,127,699 A | 11/1978 | Aumiller et al. |
| 4,906,596 A | 3/1990 | Joslin et al. |
| 5,006,575 A | 4/1991 | Chan |
| 5,255,979 A | 10/1993 | Ferrari |
| 5,265,579 A | 11/1993 | Ferrari |
| 5,331,040 A | 7/1994 | Lee |
| 5,348,397 A | 9/1994 | Ferrari |
| 5,571,165 A | 11/1996 | Ferrari |
| 5,733,324 A | 3/1998 | Ferrari |
| 5,824,033 A | 10/1998 | Ferrari |
| 6,600,957 B2 * | 7/2003 | Gadsby ............... 607/142 |
| 7,187,985 B2 | 3/2007 | Carim |

* cited by examiner

Primary Examiner—Carl H. Layno
Assistant Examiner—Yun Haeng Lee
(74) Attorney, Agent, or Firm—Cook, Alex, McFarron, Manzo, Cummings & Mehler, Ltd.

(57) ABSTRACT

A transcutaneous electrode is disclosed having a sheet electrode of an electrically-conductive material with an electrically conductive layer affixed to a major portion of the lower surface thereof. A pad of electrically-conductive gel is applied to the lower surface of the sheet electrode over the electrically-conductive layer. An electrical conductor having an unsheathed end portion is secured to the upper surface of the sheet electrode by an electrically-conductive adhesive. A high dielectric cover overlays the end out portion of the electrical conductor, and is secured to the sheet electrode by the conductive adhesive. A method for making the electrode is also disclosed.

15 Claims, 1 Drawing Sheet

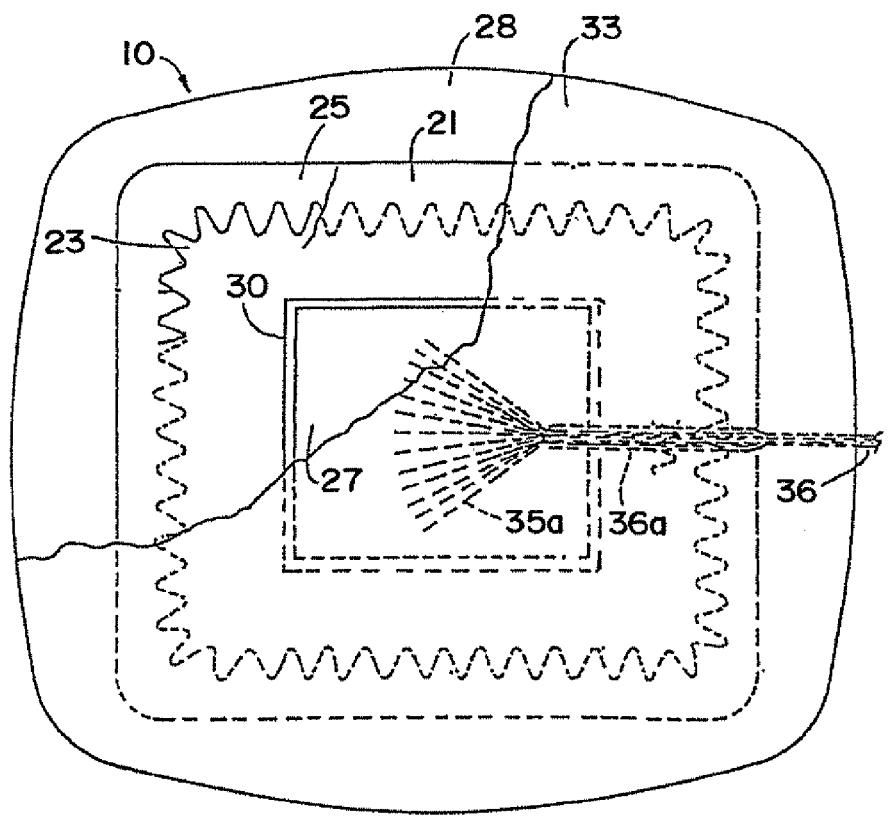
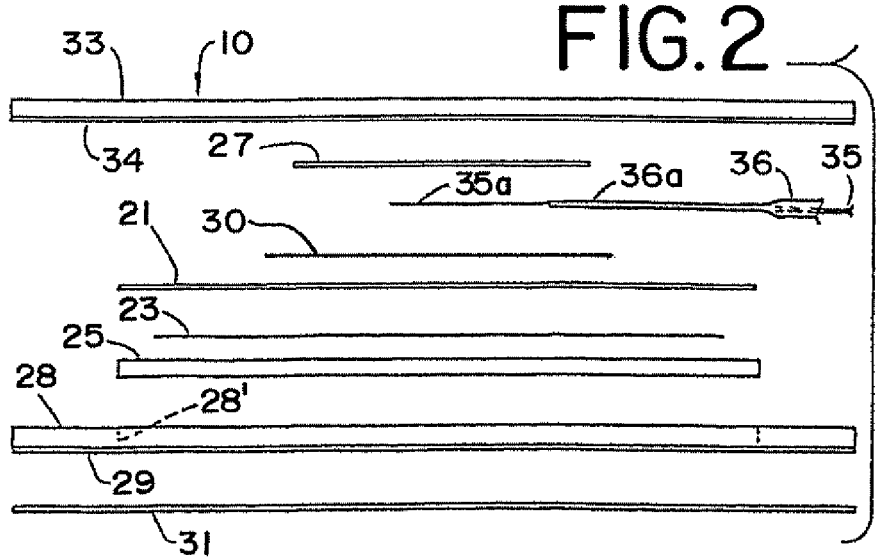

MULTIFUNCTION ELECTRODE AND METHOD OF MAKING SAME

FIELD OF INVENTION

The present application relates to a multifunction electrode that is X-ray transmissive and may be used for defibrillating and monitoring, and for a method of making the same.

BACKGROUND OF THE INVENTION

In my prior U.S. Pat. Nos. 5,571,165, 5,733,324, and 5,824,033, which are incorporated herein by reference, I have disclosed disposable transcutaneous electrodes which are X-ray transparent and capable of conducting energy sufficient for defibrillation, as well as being capable of monitoring. These electrodes have an improved current density distribution between the electrode and the skin surface of the patient to efficiently deliver the energy without burning the patient's skin.

The patents more specifically disclose electrodes comprising a polymeric sheet member having an electrically conductive metal/metal chloride coating on a lower side thereof, a pad of electrically conductive gel underlying the polymeric sheet member, and a current distributing mat affixed to the sheet member and conductively connected to the metal/metal chloride coating. The current distributing mat is configured to be electrically conductive both along and transverse to the surface of the mat so as to transfer and distribute energy to the metal/metal chloride coating of the sheet electrode member. In one embodiment, the current distributing mat includes an open mesh metallized carbon fiber web having a carbon impregnated pressure sensitive adhesive composition on the upper and lower sides of the web. In a further embodiment, the current distributing mat comprises a conductive metal foil coated on its upper and lower sides with a conductive polymer adhesive.

The metal/metal chloride coated portion of the polymeric sheet member has an area sufficiently large to achieve adequate current density distribution between the electrode and the skin of the patient. The conductive mat has an area smaller than the area of the metal/metal chloride coating. The metal/metal chloride coating on the underside of the polymeric sheet has an outer perimeter that is configured to reduce the current density at the outer perimeter of the electrode member.

Electrical energy is conducted to or from the upper surface of the conductive mat and a medical device. In applications where radio translucency of the wires is important, the wires may be advantageously formed of an X-ray transparent metal coated carbon fiber tow. For applications in which radio translucency of the conductors is not essential, the conductors may be multi-strand metal wires in which the strands can be spread out and bonded to the upper surface of the mat. Alternatively, a reinforced metallic tab or a metallic or conductive plastic post stud may be used for the conductor.

One of the difficulties in the manufacturing of electrodes, including those described above, has been the attachment of the current-carrying wire to the electrode body. Prior to the inventions disclosed in my above-identified patents, the standard method of wire attachment was a wire crimp connection to the current-carrying wire from the defibrillation equipment. While this method is still used by some manufacturers, its use is more likely to result in patient burns and an increased risk of failure of the defibrillation electrode. This was solved in the electrodes disclosed in my patents by utilizing the current distributing mat. The current distributing mat transfers normally high levels of electricity from the current-carrying wire through the electrode body and conductive gel so that the resultant electrode meets and exceeds all applicable AAMI and medical FDA standards. However, while this wire attachment method has proven to work very well, has been difficult to automate. The process of encapsulating the current-carrying wire and placing it on the electrode body is presently a hand process, which is both time consuming and expensive.

Accordingly, it is an object of the present invention to provide a medical electrode in which the current-carrying wire is secured thereto in a manner that both provides for an even current distribution and is susceptible to automation.

SUMMARY OF THE INVENTION

These objects, and others which will become apparent upon reference to the following detailed description and accompanying drawings, are achieved by a transcutaneous electrode having a sheet electrode of an electrically-conductive material with an electrically conductive layer affixed to a major portion of the lower surface thereof. A pad of electrically-conductive gel is applied to the lower surface of the sheet electrode over the electrically-conductive layer. An electrical conductor having an unsheathed end portion is secured to the upper surface of the sheet electrode by an electrically-conductive adhesive. A high dielectric cover overlays the end out portion of the electrical conductor, and is secured to the sheet electrode by the conductive adhesive.

A method for manufacturing such an electrode is also provided in which a sheet electrode is provided, the lower surface having a conductive coating applied thereto. A conductive adhesive is applied to the upper surface of the sheet electrode and the unsheathed end of a current carrying wire is placed on the upper surface of the sheet electrode so as to embed the strands of the wire in the adhesive. A high dielectric cover is applied to the upper surface of the sheet electrode and the unsheathed end of the current carrying wire and is secured to the sheet electrode by means of the conductive adhesive.

BRIEF DESCRIPTION OF THE DRAWINGS

FIG. 1 is a top plan view of the electrode according to the present invention, with certain layers cut away to illustrate details of intermediate layers.

FIG. 2 is an exploded longitudinal sectional view of the electrode of FIG. 1.

DETAILED DESCRIPTION

An exploded view of a disposable transcutaneous electrode 10 embodying the present invention is illustrated in the drawings. In general, the electrode 10 comprises a sheet electrode member 21 of electrically conductive material; an electrically conductive metal/metal chloride coating 23 on at least a major portion of the lower side of the electrode member; and a pad of electrically conductive gel 25 underlying the metal/metal chloride coating on the lower side of the electrode member. In accordance with the invention, a current-carrying wire 35 is conductively adhered to the upper side of the sheet electrode member for conducting energy to or from the upper side of the electrode member, as will be described below in greater detail.

The electrode member 21 is preferably formed of a thin flexible sheet of an X-ray transparent, electrically conductive polymer film, such as graphite-filled polyvinyl chloride film, preferably having a thickness of the order of two to four mils. An example of carbon-filled polymer which can be used is a thin carbon-filled PVC available from Burkhardt/Freeman, Holyoke, Mass., under the trademark "Conduction." Alternatively, a thin flexible sheet of tin may be substituted for the polymer film. A coating 23 of metal/metal chloride (preferably silver/sliver chloride) is applied in a layer or layers to the lower face of the electrode member as by silk screening or by flexographic printing.

The gel pad 25 is preferably a skin-compatible hydrogel having good ability to retain moisture content and adhesive tack. The gel pad 25 adhesively connects the electrode member to the patient's skin. The gel may comprise, for example, a hydrogel marketed by Ludlow Technical Products division of Tyco International Corporation, under the trademark "Procam", product number RG73P.

It is also desirable to laterally confine the gel pad 25 during storage and use. To this end, the gel pad is preferably disposed within an opening 28' in a base frame 28 of an X-ray transparent, electrically-insulative foam (such as 0.08 to 0.16 cm thick PE foam). A removable release carrier sheet 31, for example of PTFE, is attached to the underside of the base frame 28 by a skin-compatible adhesive coating 29 on the underside of the base frame. The adhesive 29 on the underside of the base frame 28 aids in adhering the electrode member to the patient's skin during use. The carrier sheet 31 underlies the gel pad 25 and covers the latter prior to use.

An electrically-insulative cover sheet 33 of X-ray transparent foam (such as 0.08 cm to 0.16 cm thick PE foam) may overlie the electrode member 21 and is adhered by an adhesive layer 34 to the upper side of the base frame 28. Alternatively, the frame 28 could be omitted and the adhesive layer on the outer periphery of the cover sheet 33 used to adhere the electrode to the patient's skin.

A current-carrying wire is provided for conducting energy to and from the upper side of the sheet electrode 21 and a medical device. In the illustrated embodiment, the current-carrying wire comprises an electrical conductor 35 having an electrically insulative sheath 36a and an unsheathed end portion 35a that is conductively adhered to the upper side of the sheet electrode, as will be described in detail below.

In some applications it is desirable that the conductors be X-ray transparent. X-ray transparent conductors are preferably formed of metallized carbon fiber tows with an insulating sheath formed of an X-ray transparent material. The carbon fiber tows are preferably of a size having between 3,000 to 12,000 fibers and plated with a metal coating that is about 20% to 50% by weight of the metal-plated carbon fiber tow. The higher-weight plating on the larger size tows provides improved current carrying capacity for repeated defibrillation pulses.

Standard carbon fiber tows are made from a polyacrylonitrile precursor and are referred to as pan base carbon fiber and are commercially available from Amoco Performance Products, Inc., Atlanta, Ga. In general, the carbon fiber tows are made by procedures described in U.S. Pat. No. 3,677,705 by heating polymeric fiber, e.g. acrylonitrile polymers or copolymers, in two stages, one to remove volatiles and carbonize and the other to convert amorphous carbon into crystal and carbon. During such procedures, the carbon changes from amorphous to single crystal and then orients into fibrous carbon. The fibrous carbon has a fiber diameter in the range of about 5 to 8 microns and the number of fibers in the tow can vary in a wide range from a few hundred to many thousand.

The carbon fiber tows can be metal plated or coated by vacuum deposition as disclosed in U.S. Pat. No. 4,132,828; by vapor deposition as disclosed in U.S. Pat. No. 3,733,213; by electroplating as disclosed in U.S. Pat. No. 4,661,403; or by chemical vapor deposition such as by thermo decomposition of nickel carbonyl gas.

In electrode applications where X-ray transparency of the conductors is not required, the conductors can be formed of metal, preferably multi-stand conductors which can be spread out, to increase the contact area between the conductor and the sheet electrode. When metal conductors are used, the electrode remains X-ray transparent, and only the metal wires and to a lesser extent the sheath, show up on the X-rays.

In keeping with one aspect of the invention, the conductor is secured to the upper surface of the sheet electrode by an electrically-conductive, pressure-sensitive adhesive 30. The electrically-conductive adhesive 30 comprises a urethane base that is impregnated with conductive beads or particles of carbon or graphite and metals, such as silver or titanium carbide, for conductivity. Preferably, the adhesive has a sheet resistance of less than 1 ohm/sq.in./mil. One such electrically-conductive adhesive is described in U.S. Pat. No. 4,127,699, which is incorporated by reference herein. Conductive adhesives suitable for use in the invention may be obtained form Electron Microscopy Sciences of Hatfield, Pa., identified as "silver conductive coating 18DB70X," "silver conductive adhesive fluid 504," and "silver conductive adhesive paste 478SS". The adhesive is applied to a selected area on the upper surface of the sheet electrode 21 by, e.g., screen printing, pad printing, flexi-graphic printing or the like, and then cured by, e.g., the application of heat, ultraviolet light, etc. The adhesive may be applied to a thickness of from approximately 1 mil. to 2 mil., which cures down to a thickness of less than 1 mil.

The unsheathed end portion 35a of the conductor is preferably spread or fanned-out, as shown in FIG. 1, and pressed into the conductive adhesive against the upper side of the sheet electrode to electrically connect the conductor to the electrode member 21. The sheath 36 is preferably heat softened and flattened over a length indicated at 36a sufficient to extend outwardly beyond the perimeter of the electrode 21 but inwardly of the perimeter of the cover prior to attachment of the conductor to the sheet electrode to minimize displacement of the gel pad.

In keeping with another aspect of the invention, a dielectric layer 27 is secured to the upper surface of the sheet electrode by the adhesive 30 so as to overlie the fanned-out conductor. The dielectric layer 27 provides structural reinforcement of the attachment of the conductor to the electrode and preferably comprises a nylon, vinyl, styrene, polyester, polyolefin, or polyethylene sheet material having a thickness on the order of 0.005 inch. Suitable sheet dielectric films are available from, e.g., the Plastics and Adhesives division of Tyco International Ltd. If comprising polyethylene, the material is preferably a closed cell polypropylene foam. The layer 27 has a high dielectric value of preferably greater than 500,000 ohms. Optionally, the side of the sheet dielectric 27 that is in contact with the sheet electrode 21 may have a conductive pressure sensitive adhesive pre-applied thereto to enhance the bond between the sheet dielectric 27 and the sheet electrode 21.

Thus, a multifunction electrode and a method of making it has been provided that meets the objects of the present invention. While the invention has been described in terms of a preferred embodiment and method, there is no intent to limit it to the same. Instead, the invention is defined by the scope of the following claims.

What is claimed is:

1. A method for attaching a current-carrying wire having a plurality of strands to an electrode body comprising:

providing a sheet electrode with an upper surface and a lower surface, the lower surface having a conductive coating applied thereto;

applying a conductive adhesive to the upper surface of the sheet electrode;

placing an end of the current-carrying wire on the upper surface of the sheet electrode to embed the strands of the wire in the adhesive; and securing a high dielectric sheet to the upper surface of the sheet electrode over the end of the current-carrying wire by means of the conductive adhesive;

whereby the electrode is capable of delivering multiple sets of defibrillation shocks.

2. The method of claim 1 wherein the adhesive is selected from the group comprising silver/carbon, metallic/carbon, and metallic adhesives.

3. The method of claim 2 wherein the adhesive comprises a urethane base.

4. The method of claim 1 wherein the adhesive is applied by screen printing.

5. The method of claim 1 wherein the adhesive is applied by pad printing.

6. The method of claim 1 wherein the adhesive is applied by flexi-graphic printing.

7. The method of claim 1 wherein the adhesive is cured after application to the sheet electrode.

8. The method of claim 7 wherein the adhesive is cured by ultraviolet light.

9. The method of claim 7 wherein the adhesive is cured by heating.

10. The method of claim 1 wherein the dielectric layer has a pressure-sensitive electrically conductive adhesive applied thereto prior to its securement to the sheet electrode.

11. A transcutaneous electrode comprising:

a sheet electrode of an electrically-conductive material having an upper and lower surface, at least a portion of the upper surface having a coating of an electrically-conductive adhesive;

an electrically-conductive layer affixed to a major portion of the lower surface of the sheet electrode;

a pad of electrically-conductive gel applied to the lower surface of the sheet electrode over the electrically-conductive layer;

an electrical-conductor having a fanned-out unsheathed end portion secured to the upper surface of the sheet electrode by the electrically-conductive adhesive; and a high di-electric cover overlying the fanned-out unsheathed portion of the electrical conductor and secured to the sheet electrode by the electrically-conductive adhesive;

wherein the transcutaneous electrode is capable of delivering multiple sets of defibrillation shocks.

12. The electrode of claim 11 wherein the adhesive is selected from the group comprising silver/carbon, metallic/carbon, and metallic adhesives.

13. The electrode of claim 12 wherein the adhesive comprises a urethane base.

14. The electrode of claim 11 wherein the high dielectric cover comprises a sheet made from the group comprising nylon, vinyl, styrene, polyester, and polyethylene.

15. The electrode of claim 11 in which the coating of the electrically conductive adhesive on the upper surface of the sheet electrode has a cured thickness of less than 1 mil.

* * * * *